United States Patent
Kutra et al.

(10) Patent No.: US 11,213,247 B2
(45) Date of Patent: Jan. 4, 2022

(54) GENERATION AND PERSONALIZATION OF A STATISTICAL BREAST MODEL

(71) Applicant: KONINKLIJKE PHILIPS N.V., Eindhoven (NL)

(72) Inventors: Dominik Benjamin Kutra, Karlsruhe (DE); Thomas Buelow, Grosshansdorf (DE); Joerg Sabczynski, Norderstedt (DE); Kirsten Regina Meetz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 28 days.

(21) Appl. No.: 16/312,808

(22) PCT Filed: Jun. 29, 2017

(86) PCT No.: PCT/EP2017/066207
§ 371 (c)(1),
(2) Date: Dec. 21, 2018

(87) PCT Pub. No.: WO2018/002265
PCT Pub. Date: Jan. 4, 2018

(65) Prior Publication Data
US 2019/0313961 A1    Oct. 17, 2019

(30) Foreign Application Priority Data
Jun. 30, 2016    (EP) .................................. 16177060

(51) Int. Cl.
*A61B 5/00*    (2006.01)
*G16H 10/60*    (2018.01)
(Continued)

(52) U.S. Cl.
CPC .......... *A61B 5/4312* (2013.01); *G06T 7/0012* (2013.01); *G16H 10/60* (2018.01);
(Continued)

(58) Field of Classification Search
CPC combination set(s) only.
See application file for complete search history.

(56) References Cited

U.S. PATENT DOCUMENTS 6,351,660 B1 * 2/2002 Burke .................... A61B 8/463
                                                                    359/32
8,010,176 B2 * 8/2011 Sun ...................... A61B 5/0053
                                                                    600/407
(Continued)

FOREIGN PATENT DOCUMENTS

EP          2793188 A2    10/2014
JP       2008129506 A     6/2008
(Continued)

OTHER PUBLICATIONS

K. Bliznakova, et al., "A three-dimensional breast software phantom for mammography simulation," Phys. Med. Biol., vol. 48, No. 22, p. 3699, 2003. (Abstract).
(Continued)

*Primary Examiner* — Tsung Yin Tsai

(57) ABSTRACT

An image processing system, comprising an input interface (IN) for receiving a plurality of input images acquired of test objects. The system further comprises a material type analyzer (MTA) configured to produce material type readings at corresponding locations across said input images (IM(CH)). A statistical module (SM) of the system is configured to determine based on said readings an estimate for a probability distribution of material type for said corresponding locations.

17 Claims, 2 Drawing Sheets

(51) Int. Cl.
   *G16H 30/20* (2018.01)
   *A61B 5/055* (2006.01)
   *G06T 7/00* (2017.01)
   *A61B 6/00* (2006.01)
(52) U.S. Cl.
   CPC .............. *G16H 30/20* (2018.01); *A61B 5/055* (2013.01); *A61B 6/502* (2013.01); *A61B 6/5205* (2013.01); *A61B 6/5211* (2013.01); *A61B 2576/02* (2013.01)

(56) References Cited

U.S. PATENT DOCUMENTS

| | | | |
|---|---|---|---|
| 9,597,046 B2 * | 3/2017 | Goossen | A61B 5/0091 |
| 2004/0234113 A1 * | 11/2004 | Miga | G06T 7/0012 |
| | | | 382/128 |
| 2005/0135664 A1 * | 6/2005 | Kaufhold | G06T 11/006 |
| | | | 382/131 |
| 2010/0295848 A1 | 11/2010 | Grewer | |
| 2011/0216951 A1 * | 9/2011 | Ye | G06T 7/0012 |
| | | | 382/128 |
| 2012/0114213 A1 | 5/2012 | Buelow et al. | |
| 2012/0130490 A1 | 5/2012 | Erni et al. | |
| 2012/0301003 A1 | 11/2012 | Erhard et al. | |
| 2013/0018591 A1 * | 1/2013 | Grzegorczyk | G01N 22/00 |
| | | | 702/19 |
| 2013/0023436 A1 | 1/2013 | Jones et al. | |
| 2014/0064587 A1 * | 3/2014 | Johnson | A61B 6/12 |
| | | | 382/131 |
| 2014/0219500 A1 | 8/2014 | Moehrle et al. | |
| 2014/0222443 A1 * | 8/2014 | Danenberg | G01N 33/57407 |
| | | | 705/2 |
| 2014/0348404 A1 * | 11/2014 | Jerebko | G06T 7/33 |
| | | | 382/131 |
| 2014/0371570 A1 * | 12/2014 | Davis | A61B 6/469 |
| | | | 600/407 |
| 2015/0161786 A1 | 6/2015 | Seifert | |
| 2015/0305652 A1 | 10/2015 | Angott | |
| 2016/0012582 A1 * | 1/2016 | Mauldin, Jr. | G06T 11/60 |
| | | | 382/131 |
| 2017/0181808 A1 * | 6/2017 | Panescu | A61B 34/32 |
| 2017/0360578 A1 * | 12/2017 | Shin | B33Y 50/00 |

FOREIGN PATENT DOCUMENTS

| | | |
|---|---|---|
| WO | 0014668 A1 | 3/2000 |
| WO | 2013038284 A1 | 3/2013 |
| WO | 2014206881 A1 | 12/2014 |
| WO | 2016072926 A1 | 5/2016 |

OTHER PUBLICATIONS

D. Kutra, et al., "An anatomically oriented breast coordinate system for MRI," in SPIE Medical Imaging, 2015. (Absract).

Albert Gubern-Mérida, et al.: "Breast Segmentation and Density Estimation in Breast MRI: A Fully Automatic Framework", January 2015IEEE Journal of Biomedical and Health Informatics 19(1):349-57.

Kawaguchi, et al.: "Generation of attenuation correction factor for PET from a T1-weighted pelvic MR image using hybrid-segmentation and atlas method", 2015, no English translation.

Koon, et al.: "Quantitative analysis of group-specific brain tissue probability map for schizophrenic patients", 2005.

* cited by examiner

GENERATION AND PERSONALIZATION OF A STATISTICAL BREAST MODEL

This application is the U.S. National Phase application under 35 U.S.C. § 371 of International Application No. PCT/EP2017/066207, filed on Jun. 29, 2017, which claims the benefit of European Application Serial No. 16177060.7, filed Jun. 30, 2016. These applications are hereby incorporated by reference herein.

FIELD OF THE INVENTION

The invention relates to an image processing system, to an image processing method, to a computer program element and to a computer readable medium.

BACKGROUND OF THE INVENTION

Biomechanical simulations of the breast can be used to simulate the breast in different patient positions such as prone, supine, or upright. More recently, biomechanical models have been also used in the simulation of surgery. Such applications require an elaborate geometric model of the breast. This is usually generated from MR imaging, a costly and time consuming procedure. Given the spread of breast cancer and the fact that MRI is not a standard imaging modality, only a fraction of affected patients can benefit from pre-surgical simulations as a decision aid.

SUMMARY OF THE INVENTION

There may therefore be a need for a system or method to at least partly address the above shortcomings.

The object of the present invention is solved by the subject matter of the independent claims where further embodiments are incorporated in the dependent claims. It should be noted that the following described aspect of the invention equally applies to the image processing method, to the computer program element and to the computer readable medium.

According to a first aspect of the invention there is provided an image processing system, comprising;
an input interface for receiving a plurality of input images acquired of test objects;
a material type analyzer configured to produce material type readings at corresponding locations across said input images; and
a statistical module configured to determine based on said readings an estimate for a probability distribution of material type for said corresponding locations.

According to one embodiment, the system comprises a correlator configured to correlate the probability distribution estimate with meta-data of said test objects to obtain a parameterized probability distribution estimate for said corresponding locations.

According to one embodiment, the system comprises a spatial correspondence component configured to establish said corresponding locations based on coordinates in respective coordinate systems for said images, said respective coordinate systems derived from a common geometric model.

According to one embodiment said respective coordinate systems are configured to reflect one or more symmetries in said test objects.

According to one embodiment, the system comprises a material type estimator configured to produce a material type estimate for a given location in a given image of an object of interest based on said parameterized probability distribution estimate.

According to one embodiment, said input images have been previously acquired by an imaging apparatus capable of soft-tissue discrimination.

According to one embodiment, said test objects include mammal (in particular a human female) breasts of different subjects.

According to a further aspect, there is provided an image processing method, comprising the steps of:
receiving a plurality of input images acquired of test objects;
producing material type readings at corresponding locations across said input images; and
determining, based on said readings, an estimate for a probability distribution of material type for said corresponding locations.

According to one embodiment, the method comprises:
correlating the probability distribution estimate with meta-data of said test objects to obtain a parameterized probability distribution estimate for said corresponding locations.

According to one embodiment, the said corresponding locations are established based on coordinates in respective coordinate systems for said images, said respective coordinate systems derived from a common geometric model.

According to one embodiment the method comprises:
estimating a material type for a given location in a given image of an object of interest based on said parameterized probability distribution estimate.

According to a further aspect, there is provided a computer program element which, when being executed by a processing unit, is adapted to perform the above mentioned method steps.

According to a yet further aspect, there is provide a computer readable medium having stored thereon the said program element.

The proposed method and system allow accounting for the relatively high variability (in shape and composition) of the female breast. The proposed method and system allows generating in a structured manner virtual breast models that can be truly personalized/adapted to any given patient without mere, generic heuristic assumptions about the internal tissue distribution. Such mere heuristics can be avoided which in turn yields more realistic models and thus more realistic bio-mechanical simulations.

The proposed method and system allows generating a distribution of tissue types as it can be observed in real patients. The generation tissue type distribution is not ad hoc or "random" but is driven by anatomical knowledge incorporated in the general statistical model for the object of interest (e.g., breast) as trained from the test objects ("cohort").

In sum, the proposed approach, when applied to breast imaging as mainly envisaged herein, includes training a statistical distribution model of breast tissue within a population using high resolution modalities like MRI and CT. By mapping each breast onto a standard breast model, it is possible to generate a model of the spatial distribution of tissue. This tissue distribution model is correlated with meta-information from the same population like e.g. BMI, age, height, menopausal status, as well as information derived from low-cost modalities (e.g. 3D scans, photography, mammography, tomosynthesis). By using such information of a specific patient, not part of the training cohort, the statistical model can later be personalized into a personalized breast model with appropriate size and tissue distribution. Such a personalized model enables for instance patient specific biomechanical modelling of the breast without the need, at the personalization stage, of expensive, tissue-discriminating modalities like MRI.

BRIEF DESCRIPTION OF THE DRAWINGS

Exemplary embodiments of the invention will now be described with reference to the following drawings (not necessarily to scale) wherein.

DETAILED DESCRIPTION OF EMBODIMENTS

Figure 1:
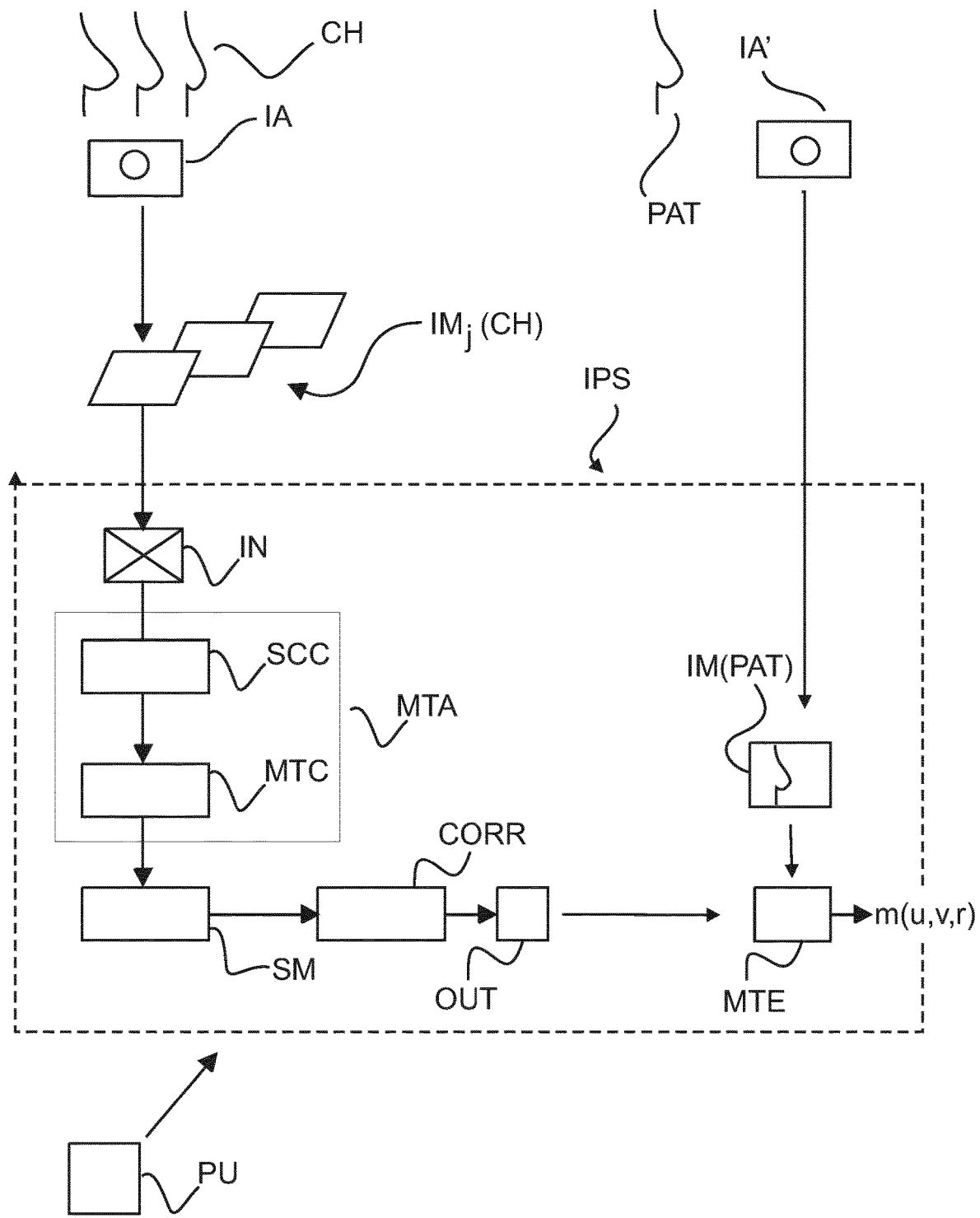
FIG. 1 shows a block diagram of an image processing system.

With initial reference to FIG. 1, there is shown a schematic block diagram of an image processing system as proposed herein.

Broadly, the image processing system IPS is configured to produced, based on input imagery of an anatomy of interest, a generalized statistical model of said anatomy which can then be optionally personalized to a given patient PAT. In one embodiment, but not necessarily all embodiments, the anatomy is a human female breast although other anatomies are also envisaged herein. Also, applications of the proposed image processing system to contexts other than medical are also envisaged.

The general statistical breast model is essentially a spatially resolved family or collection of probability distributions for tissue type. These distributions can be personalized based on meta-data such as age, weight etc., of a given patient PAT. The general statistical model or its personalized version can be used as input model for biomechanical simulations. The availability of a precise estimate for the spatial distribution of tissue types allows for realistic biomechanical simulations as different tissue types react differently to mechanical loads.

The components or modules of the image processing system IPS may be implemented as software routines that are programmed to cooperate in a single software suite. The system IPS can be run on a general purpose computing unit PU such as a workstation associated with an imager IM or on a server computer associated with a group of imagers. Alternatively the components of the image processing system IPS may be arranged in a distributed architecture and connected in a suitable wired or wireless communication network. Alternatively, some or all components of the image processing system may be arranged in hardware such as a suitably programmed FPGA (field-programmable-gate-array) or as hardwired IC chip.

Referring now in more detail to FIG. 1, at input port IN of the image processing system, input imagery IMACH) of a cohort of patients CH are received, not necessarily at the same time. The imagery has been previously acquired by one or more imagers IA. Preferably the input imagery IMCH has been acquired by imager(s) IA that are capable of soft tissue discrimination, such as a magnetic resonance imager or a phase contrast imaging or other.

The input imagery IMCH from the patient cohorts CH can be retrieved for instance from a picture archive systems PACS in a hospital information systems HIS etc. In others, historical soft tissue imaging data acquired in the past from different patients may be used. As explained in more detail below, this historical input imagery serves as a training corpus to contrast the statistical breast model. Preferably, but not necessarily the imagery is of the DICOM type. DICOM imagery has meta-data of the respective patients encoded therein in a header file of the respective image file. This meta-data may be used, as will be explained in more detail below, to personalize the general model to a specific, given patient. The patients in the cohort CH may be viewed herein as test objects that represent the same object or anatomy class, in this case, that of a female breast for which the generalized statistical model is to be built.

As indicated, the input imagery is used to train a statistical distribution model of breast tissue within a population of which the cohort is a sample. The statistical breast model produced herein can be expected to be more accurate the larger this sample is. It has been observed that picking a cohort randomly from women in the order of hundreds or thousands of images produces results of sufficient quality. In one exemplary embodiment, about 100 images are used. It should be understood that the following processing of the input imagery IM(CH)) is not necessarily a one-off operation although this is still envisaged if a sufficient number of training imagery is available from the start. More often, however, one will start with a certain initial set of input imagery IM(CH), and the model can then be refined and the processing described below can be repeated to take into account newly available input imagery.

The system IPS comprises a material type analyzer MTA. The material type analyzer includes a material type identifier component MTC and a spatial correspondence component SCC.

The spatial correspondence component SCC of the system IPS operates to establish respective sets of corresponding anatomical locations within the input cohort imagery IM(CH) where the material type analyzer collects material type readings. In other words, the analyzer determines which type of material (in particular which type of tissue) the image location represents.

Referring now first in more detail to the spatial correspondence component SCC, in one embodiment the spatial or anatomical correspondence is established by transforming world coordinates of locations in the input imagery into coordinates expressed in respective co-ordinate systems that correspond to the symmetry of the anatomy considered. For instance, for the human-female breast, a semi-ellipsoidal co-ordinate system as proposed in D Kutra et al "An anatomically oriented breast model for MRI", *Proc. SPIE* 9415, Medical Imaging 2015: Image-Guided Procedures, Robotic Interventions, and Modeling, p 941521 (Mar. 18, 2015), has shown to yield good results and is envisaged herein in a preferred embodiment. When other anatomies are or interest, different co-ordinate systems having different symmetries may be called for instead. Each of the respective coordinate systems have been derived by fitting the same shape model (geometric primitive) to the respective images in individual fitting operations (as will be explained in more detail below). These respective image coordinate systems are thus adapted to the respective geometry/symmetry as encoded in the respective input image IM(CH). Expressing image locations in each image in terms of coordinates of their respectively adapted coordinate system allows establishing spatio-anatomic correspondences across the images. Specifically, the spatial correspondence component SCC allows finding the spatial coordinates of the same anatomical feature across the input imagery. For instance, the respective location of the mammilla in each of the images can be specified, and similar for any other anatomical location. The same (hence, corresponding) feature or anatomic location can be expected to have the same coordinates in each respective coordinate system of image of the input imagery IMCH. For instance, a given location with coordinates (u,v,r), with u being the polar component and v the azimuth and r the radial component in the semi-ellipsoidal coordinate system as proposed by Kutra et al (supra), can be expected to designate the same anatomic feature in the cohort breasts. It should be noted however that establishing the anatomical correspondence across the input imagery by way of an anatomy-symmetry-adapted coordinate systems is, although preferred, merely one possible embodiment among others. For instance, instead, a user may specify by mouse-click into the imagery or by any other designation tool, those locations that are deemed to represent said anatomic correspondences.

With continued reference to operation of the spatial correspondence component, this includes, as mentioned, fitting a geometric primitive (such as a semi-ellipsoid) separately to each of the input images IM(CH) to derived the respective geometrically adapted image coordinate systems. The respectively fitted geometric primitive approximates the shape of the breast as encoded in the respective input image. The fitting operation establishes anatomical inter-patient correspondence of the different patient images in the cohort by matching geometric features of the geometric primitive with image structures that represent suitable anatomic parts. For instance, one may fit a tip of the semi-ellipsoidal model to the mammilla portions of the image and the posterior border part of the semi-ellipsoidal model to the image structure representative of the pectoral muscle. In this manner different parts of the primitive geometrical model are fixed to different salient anatomical locations in the input imagery. Because the same primitive geometry is used for the fitting, the anatomical correspondence can be stablished. To achieve a yet better fit, the models may be deformed by free-form deformation or similar. In other words, in general the fitting operation involves non-rigid transformations.

World coordinates of the pixel or voxel locations representing the various tissue types in the respective input images IM(CH) are transformed by the spatial correspondence component SCC into geometrically intrinsic parameters of the geometrical primitive, such as the triple (u,v,r) in case of the embodiment where the primitive is the (semi)ellipsoid. These parameters define the coordinates in the respectively adapted coordinate system each based on the common geometry of the geometric primitive as used in the fitting operation. This approach allows exploiting the generated inter-patient correspondence as represented in the cohort imagery IM(CH). World coordinates include in-image coordinates (such as voxel indices) or coordinates in a suitable length unit (e.g. mm) relative to a reference frame of the imaging system(s) used to acquire the images. If the image format is in DICOM, then one can convert between these types of world coordinates into one another.

As mentioned, one way to establish the correspondence among locations in the images is to simply use the same coordinates $u=\tilde{u}$, $v=\tilde{v}$, $r=\tilde{r}$ in each image in the respectively adapted coordinate system. Alternatively, an offset $(\Delta u, v\Delta)$ may be applied to the coordinates based on the amount of rigid or non-rigid transformation experienced at the respective location when fitting the respective geometric primitives.

The fitting operation can be implemented by any known optimization scheme. For instance, an objective function can be set up as the squared sum of deviations of the breast image from the primitive. The geometric parameters of the primitive are then solved for so as to minimize the objective function. Other objective function formulations are also envisaged.

Preferably, the input images IM(CH) and the geometric primitives are 3D but applications of the proposed method to 2D imagery with fitting of 2D models is also envisaged in alternative embodiments.

The input cohort imagery IM(CH) is processed by the material type identifier component MTC. This is implemented by otherwise known automated tissue analysis/classification algorithms that allow to establish, at each location in the input imagery, a material type, for instance, a tissue type such as fat tissue, water, fibro-glandular tissue, vessel tissue, muscular tissue, etc. The tissue analysis algorithm matches image values (e.g., grey values) to known tissue characteristics. For instance, especially MRI image values can be matched to respective tissue classes.

It should be appreciated that the two tasks of material property identification and the establishing of spatial correspondence can be carried out in any order. That is, the images are first processed by the material type identifier component MTC and then by the spatial correspondence component SCC, or the other way round. Irrespective of the processing order, the (intermediate) output at the material type analyzer stage is formed from material type readings $m_j$ for each set of spatio-anatomically corresponding locations. In other words, for each set j of corresponding locations, there are N material type readings $(m_1, \ldots m_N)^j$, N being the number of images in the input imagery IM(CH). This output of spatially resolved material type readings may be stored in a matrix structure with indices j . . . J, n . . . N.

The spatially resolved material type readings are processed by a statistical module SM. The statistical module computes a respective probability distribution (or density) estimate across the given corresponding locations. This operation is then repeated for each set j of (other) corresponding locations. In other words, for each of the N sets of different corresponding locations one obtains a respective (in general different) probability distribution over tissue types. In yet other words, each of the tissue type probability distributions are "pegged" to a respective set of corresponding locations expressed in intrinsic co-ordinates in the respectively adapted co-ordinate systems for the images.

This collection or family of probability distributions allows computing the probability for there to be, for instance fat, at a given location. The respective probability distributions (or probability densities) at the different locations can be estimated in an otherwise known manner, for instance, by forming ratios of the respective tissue type readings. For instance, one looks at a number of fat occurrences across a given set of corresponding locations, and then divides this number by the total number of images considered. Other statistical methods may also be used. For instance, the local probabilities can alternatively take account conditions like age, BMI, etc. of the patient under consideration. When computing tissue probabilities, either only similar subjects (with respect to the meta-data) are taken into account or contributions of data from the test cohort can be weighted with their similarity to the patient under consideration.

Alternatively, the respective coordinates in the different adapted coordinate systems for each image are transformed in a second transformation into a common coordinate system (such as the sphere or other shape) by a further transformation stage component (not shown). The statistical module SM then operates to analyze for spatial patterns of tissue types in this common coordinate system, e.g., by using methods of spatial statistics. The second transformation to the common coordinate frame allows normalizing the tissue distributions which in turns allows an optional visualization of the distributions.

The collection of these localized probability distributions as provided by the statistical module SM stage forms a generalized statistical model of the breast. This generalized statistical model can be refined by a correlator CORR that correlates these distributions to meta-data of the patients in the patient cohort CH. The correlator CORR aims at establishing a functional relationship for how these probability distributions change with patient meta-data of the patient in the cohort, such as age, weight, BMI index etc. Any known machine learning or curve fitting algorithm, response surface methodology can be used to implement the correlator CORR stage. The functional relationship computed by the correlator CORR may be explicit (such as functional expression) or implicit such as in machine learning schemes such as neural networks, where the sought after functional relationships is encoded in the weights assigned to neural network nodes in different layers.

The output of the correlator CORR forms a parameterized family of the spatially located probability distributions obtained earlier. Each parameter α represents a different meta-data combination and these parameterized probability distributions Fα (in particular densities fα) are then output at the output port OUT and can be used to personalize a given image IM(PAT) of a (new) patient PAT not from the cohort CH. The parameterized probability distributions produced at the correlator CORR stage may also be understood as conditional probability distributions. For instance, the probability for, say, fat at a given location is now conditioned on the fact that the patient has a certain age and/or BMI etc.

The personalization operation is achieved by a material type estimator MTE. The material type estimator MTE receives as input the new image IM(PAT) of the new patient PAT to produce a material type estimate for any given location in the new image IM(PAT). Preferably, as envisaged herein, the new image IM(PAT) has been previously acquired by a "cheaper" imaging modality IA'. Examples of such "cheap" imaging modalities include tomosynthesis, X-ray, etc. In another embodiment, the new input image IM(PAT) may be as simple as a 3D surface scan obtained by an optical scan. In other words, the input imagery IM(PAT) for the material type estimator MTE is generally of lower resolution than the cohort imagery IM(CH) and does not encode tissue type or does so to a lesser extent than the cohort imagery IM(CH) used in training the generalized statistical model.

In more detail, the new non-tissue-type-discriminating input image IM(PAT) is processed by the material type estimator MTE in a similar manner as described above, save for the tissue type analysis which is now not possible. Specifically, the geometric primitive (e.g., the semi-ellipsoid) is fitted as before purely on the geometric shape as encoded in the low cost image IM(PAT). Fitting of the primitive allows identifying locations (u,v,r) using the adapted anatomic co-ordinate system as explained above. The patient's PAT meta-data is obtained either from a DICOM header file or otherwise (e.g., by querying the patient PAT herself) and the meta-data is then used to compute, from the parameterized family of probability distribution as supplied at output port OUT, the family that matches the given meta-data of patient PAT. For each given location, expressed in intrinsic coordinates (e.g., u,v,r), an estimate m(u,v,r) can now be made of the tissue type likely to be found at the respective location. The estimate is obtained by using, from the meta-data matched family of probability distributions, the one that is associated with the given location. For instance, the material type estimator MTE may assign the tissue type that has the highest probability, given the probability distribution for the considered location. In one embodiment, in addition, the similarity of the meta-data of the patient relative to the met-data of the training data is taken into account to adjust (e.g. by weighting) of said highest probability. It will be understood from the above, that the material type estimator MTE performs a three-fold operation: i) a match against the meta-data to find the family of probability distributions, ii) a match against location from among the family of probability distributions, and iii), the actual estimate based on the probability distribution. The personalized model can then be processed to a bio-mechanical simulation package or can be stored in a memory or otherwise processed.

In sum, the cohort input imagery, derived from imaging modalities capable of tissue-discrimination, is used to learn the tissue distribution and this knowledge of the internal anatomy is provided as the generic statistical breast model. This has the benefit that one can then afford the later processed, non-cohort image, to merely have shape contrast but not (or to a lesser) extent tissue type contrast. The non-cohort image is then merely used to learn the shape of the personalized model and this is then enriched with anatomical knowledge on tissue type distribution as per the generalized statistical model.

Figure 2:
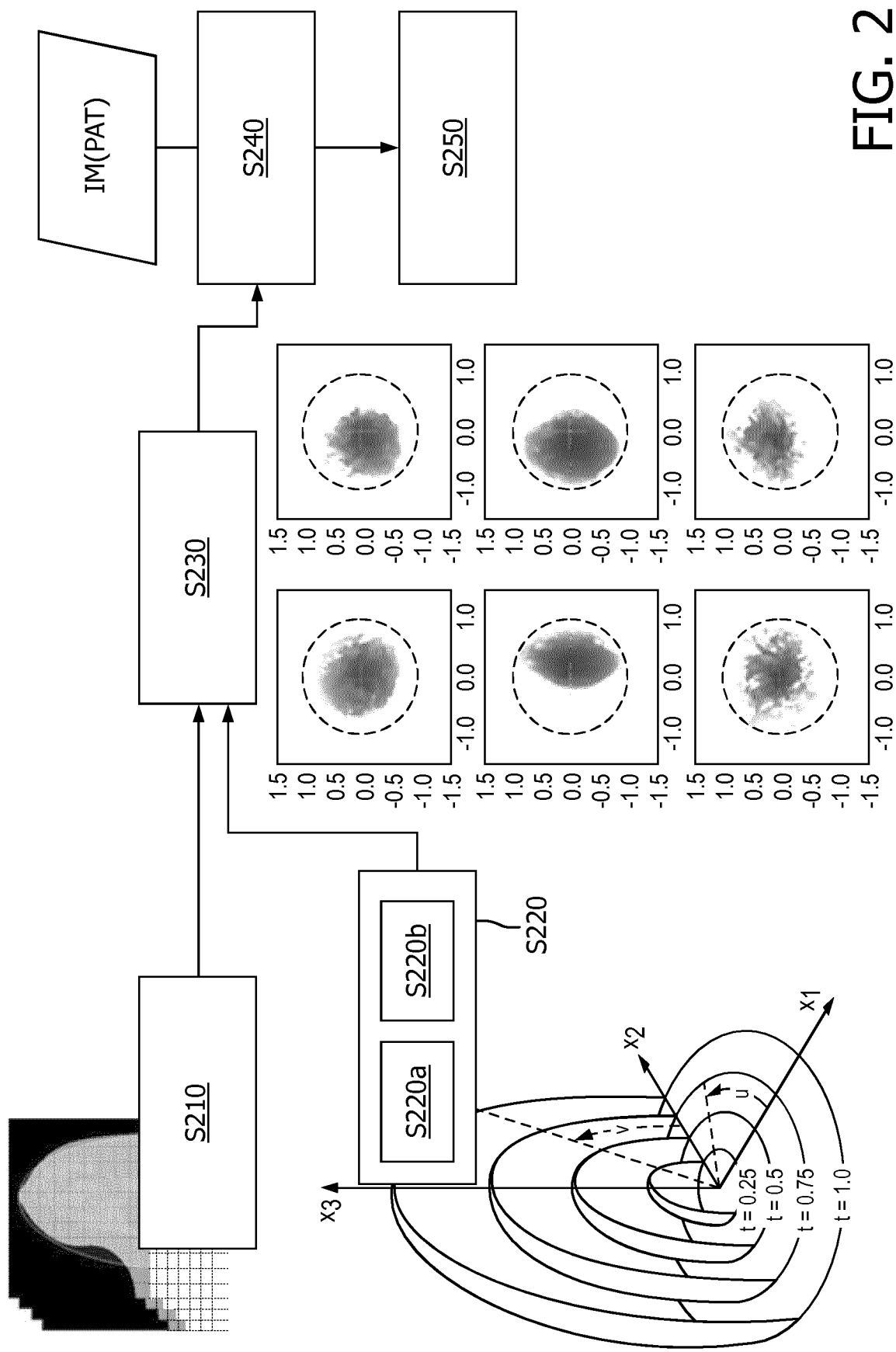
FIG. 2 shows a flow chart of a method of image processing.

Reference is now made to FIG. 2 which shows a flow chart of an image processing method underlying operation of the image processing system IPS. However, the following flow chart may also be understood in its own right and is not necessarily tied to the architecture of the image processing system IPS as per FIG. 1.

At step S210 a plurality of input cohort images acquired of test objects is received. The test objects are of the same class, such as breast or other anatomy of a plurality ("cohort") or patients. Preferably the input cohort images are acquired by an imaging modality capable of tissue discrimination.

At step S220, material property type readings are produced at corresponding locations across said input cohort images.

Step S220 includes establishing S220a anatomically corresponding locations across the input cohort images by using respective co-ordinate systems. These are derived by separately fitting a common shape model to the respective input cohort images. These co-ordinate systems are preferably adapted to one or more symmetries of the image structure representing the anatomy of interest as recorded in the input cohort imagery. Preferably, the imagery is breast images and the co-ordinate systems used are semi-ellipsoidal.

The step S220 of producing material property type readings further includes identifying S220b material types based on image values in the cohort images.

Steps S220a,S220b can be performed in any order.

At step S230 the respective probability distributions of material type are then determined based on the said readings for the corresponding locations. In this manner, for each set of corresponding locations, a respective, dedicated probability distribution estimate is obtained.

At step S240 the probability distribution determined for each set of corresponding locations is then correlated with meta-data of the test objects. The correlation step results in a set of parameterized probability estimates, each parameter representing different categories of meta-data (e.g., weight, age, BMI, etc.). The collection of parameterized probability distribution estimates for each set of corresponding locations forms a generalized statistical model trained from the test objects.

This generalized statistical model can be personalized for a specific, given image of a specific object of the same class as the test objects, but the specific object not being drawn from the test objects used to train the generalized statistical model. More specifically, the personalization operation is effected in step S250 where a material type estimate for a given location in the non-cohort image of the non-test object is obtained based on the parameterized probability distributions as obtained in the correlation operation in step S230.

Yet more specifically, step S250 comprises using metadata of the given non-test object to adapt the parameterized collection of probability distributions to the non-test object.

The so adapted collection of probability distributions is then used to estimate tissue type for the non-cohort image. For example, the tissue type having the highest probability is assigned to a given location. Specifically, in order to match location in the non-cohort image to the corresponding probability distribution (from the collection) for that location, the some geometrical shape primitive used above in step S220 can be fitted to the non-cohort image. A coordinate system based on this fitted model can then be used to specify i) the given location in the non-cohort image and ii) the adapted probability distribution from the collection for this location. Step S240 is then repeated for each location to so obtain a personalized model for the given object. In other words, the personalized model comprises the fitted shape and the internal tissue distribution as per the adapted probability distributions.

In an optional step, the personalized model is passed to a biomechanical simulation tool or may otherwise be processed.

In the above, whilst the cohort imagery includes tissue contrast, the non-cohort image does not, or does only to a lesser extent. In particular, it is sufficient that the non-cohort image merely includes shape information. In one embodiment, the non-cohort image may be as simple as a surface scan or an X-ray image whilst the cohort imagery is obtained from tissue imaging modalities, such as MRI or similar.

Preferably in the above, the input cohort imagery and the new, specific non-cohort image, are acquired with the patient assuming the same posture relative to gravity. For instance, the cohort input imagery and the new image have been acquired in prone position.

The end result of the method is a personalized anatomical software/virtual breast model comprising the outer shape of the breast in, e.g., prone position, as well as a distribution of internal structures such as fibro-glandular tissue, fat, etc. This personalized model can be used in biomechanical software simulation packages, such as finite-element packages, e.g., niftysim, FeBio or other.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing method, comprising the steps of:
receiving a plurality of input images acquired of test objects;
producing material type readings at corresponding locations across said input images; and
determining, based on said readings, an estimate for a probability distribution of material type for said corresponding locations;
wherein a probability distribution model is trained from information in the input images by automated image analysis and classification and applied to an image which does not encode tissue type or encodes tissue type to a lesser extent than the input images.

2. The method of claim 1, comprising:
correlating the probability distribution estimate with meta-data of said test objects to obtain a parameterized probability distribution estimate for said corresponding locations.

3. The method of claim 1, comprising:
estimating a material type for a given location in a given image of an object of interest based on said parameterized probability distribution estimate.

4. A non-transitory computer readable medium comprising a program element which, when being executed by a processing unit, is adapted to perform the method steps of claim 1.

5. The method according to claim 1, wherein tissue type distribution corresponding to the location in the images is learned from the determination of a probability distribution of material type for said corresponding locations.

6. The method according to claim 5, wherein the tissue type distribution is selected from the group consisting of fat tissue, water, fibro-glandular tissue, vessel tissue, and muscular tissue.

7. The method of claim 1, wherein the said corresponding locations are established based on coordinates in respective coordinate systems for said images, said respective coordinate systems derived from a common geometric model.

8. An image processing system comprising:
an input interface for receiving a plurality of input images acquired of test objects;
a material type analyzer configured to produce material type readings at corresponding locations across said input images; and
a statistical module configured to determine based on said readings an estimate for a probability distribution of material type for said corresponding locations;
wherein a probability distribution model is trained from information in the input images by automated image analysis and classification and applied to an image which does not encode tissue type or encodes tissue type to a lesser extent than the input images.

9. The system as per claim 8, comprising a spatial correspondence component configured to establish said corresponding locations based on coordinates in respective coordinate systems for said images, said respective coordinate systems derived from a common geometric model.

10. The system as per claim 9, wherein said respective coordinate systems are configured to reflect one or more symmetries in said test objects.

11. The system as per claim 8, comprising a material type estimator configured to produce a material type estimate for a given location in a given image of an object of interest based on said parameterized probability distribution estimate.

12. The system as per claim 8, said input images previously acquired by an imaging apparatus capable of soft-tissue discrimination.

13. The system as per claim 8, wherein said test objects include mammal breasts of different subjects.

14. The system according to claim 8, wherein the statistical module learns the tissue type distribution corresponding to the location in the images from the determination of a probability distribution of material type for said corresponding locations.

15. The system according to claim 14, wherein the tissue type distribution is selected from the group consisting of fat tissue, water, fibro-glandular tissue, vessel tissue, and muscular tissue.

16. The system according to claim 8, wherein the images are DICOM images and include said meta-data in a header.

17. The system as per claim 8, further comprising a spatial correspondence component configured to establish said corresponding locations based on coordinates in respective coordinate systems for said images, said respective coordinate systems derived from a common geometric model.

* * * * *